Figure 1:
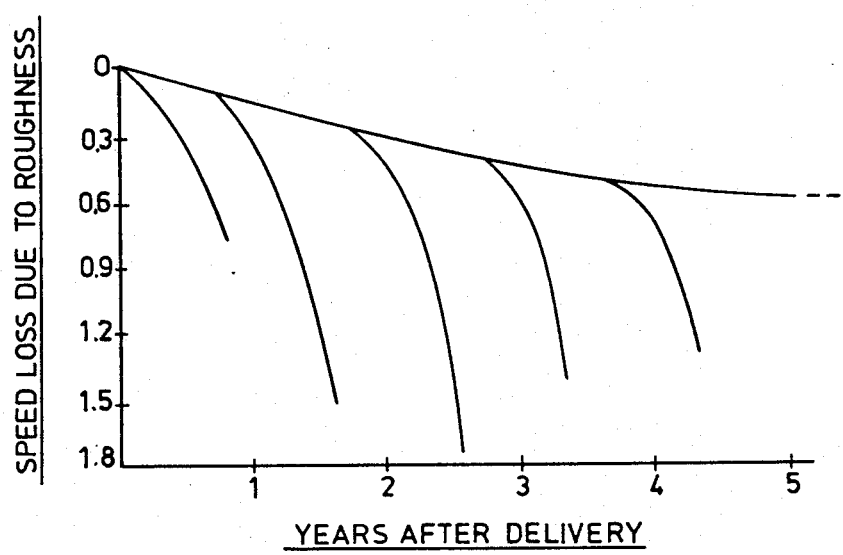

United States Patent

Milne et al.

4,021,392

May 3, 1977

[54] MARINE PAINT

[75] Inventors: Alexander Milne, Jesmond; George Hails, Whickham, both of England

[73] Assignee: The International Paint Company Limited, London, England

[22] Filed: Mar. 26, 1975

[21] Appl. No.: 562,008

[30] Foreign Application Priority Data

Apr. 3, 1974 United Kingdom ............. 14723/74

[52] U.S. Cl. ........................ 260/28.5 A; 106/15 R; 260/33.6 VA; 260/42.44; 424/81; 427/409
[51] Int. Cl.² .......................................... C08K 3/22
[58] Field of Search ... 260/42.44, 28.5 A, 33.6 VA; 424/81; 106/15 AF

[56] References Cited

UNITED STATES PATENTS

| | | | |
|---|---|---|---|
| 3,167,473 | 1/1965 | Leebrick | 424/81 |
| 3,332,789 | 7/1967 | Abbot | 106/15 AF |
| 3,702,256 | 11/1972 | Stevens | 106/15 AF |
| 3,817,759 | 6/1974 | Wessely | 106/15 AF |

*Primary Examiner*—James H. Derrington
*Attorney, Agent, or Firm*—Davis, Hoxie, Faithfull & Hapgood

[57] ABSTRACT

A top coat paint for ships' hulls comprising a. a film-forming copolymer containing from more than 50 up to 80 per cent by weight of units of at least one tri-organo tin salt of an olefinically unsaturated carboxylic acid, the balance of the copolymer being units of at least one olefinically unsaturated comonomer, b. a substantially water insoluble metalliferous pigment capable of reacting with sea-water to form a water-soluble metal compound, and c. a hydrophobic organic retarder for retarding the rate of ion exchange between sea-water and the copolymer (a), which retarder
   i. has a solubility in sea-water at 25° C of not more than 5 parts per million by weight and is miscible with the copolymer (a),
   ii. has a negligible vapour pressure at 25° C and
   iii. is present to the extent of at least 5 per cent by weight based on the weight of the tri-organo tin ion content of the copolymer (a).

The top coat paint is an anti-fouling paint which at least preserves the ship's service efficiency during the life of the top coat paint and may in some circumstances lead to an improvement in that efficiency during service. Two or more coats of the paint may be applied successively to the ship's hull the proportion of retarder decreasing from the first applied coat to the last applied coat.

9 Claims, 11 Drawing Figures

MARINE PAINT

This invention is concerned with a top coat paint for application to ships' hulls.

The growth of marine organisms on the submarine parts of a ship's hull increases the frictional resistance of the hull to passage through water, leading to increased fuel consumption and/or a reduction in the speed of the ship. Marine growths accumulate so rapidly that the remedy of cleaning and repainting as required in drydock is too expensive to contemplate. The alternative which has been practised with increasing efficiency over the years, is to limit the extent of fouling by applying to the hull a top coat paint incorporating anti-fouling agents. The anti-fouling agents are biocides which are freed from the surface of the paint over a period of concentrations lethal to marine organisms at the hull surface. The anti-fouling paint fails only when the concentration of biocide available at the paint surface falls below the lethal concentration and with modern paints up to two years of useful life is expected.

The better anti-fouling paints are thus effective in delaying the gross infestation of hulls for considerable periods, but little attention has been given to overcoming the roughness of the paint film itself which increases over that period and is not eliminated on repainting. A top coat paint on a ship's submarine surface has irregularities from its method of application and is furthermore subject to breakdown and delamination during service, increasing the roughness of the hull so that the performance of the ship falls off, even when fouling is prevented. A new ship with a freshly painted hull usually has a roughness between 75 $\mu$m and 125 $\mu$m, the roughness being the average height of peaks above troughs in the film as measured by the British Ship Research Association's (B.S.R.A.) Wall Gauge. During the service life of a ship the roughness may increase to 500 $\mu$m to 750 $\mu$m due to the onset of corrosion and deficiencies in the hull maintenance and painting process. When the roughness increases from 75 $\mu$m to 125 $\mu$m initially to 750 $\mu$m an increased shaft horse power of 40 percent is required to maintain the same speed.

Put another way, the speed of a smooth hulled ship may be reduced from 15 knots to 13.5 knots at the same shaft horsepower as the hull acquires a roughness of 750 $\mu$m.

The speed loss due to fouling and hull roughness was the subject of a paper by Mr. I. E. Telfer at the Lisbon Conference in July 1972 and his results are represented in FIG. 1 of the accompanying drawings, which is a graph showing the importance of both protection against fouling (which is itself a form of roughness) and the progressive long term roughening of the hull due to the breakdown of paint coats and the repeated recoating of the hull with conventional paints. In FIG. 1, the vertical shows the speed in knots at constant shaft horsepower and the horizontal the age of the subject vessels after delivery. The solid line shows the average performance of a number of vessels in the years following delivery and it indicates a loss of speed approximately 0.1 knot/annum due to the growing inherent roughness of the hull due to the accumulation of defects in the paint surface despite periodic applications of paint coats.

The branched sections of the graph show the effects of fouling on the performance of the vessel and indicate the repeated use of anti-fouling paints of low efficiency. When a hull fouls the drop in speed may be in the range 0.8 to 1.8 knots and on docking and repainting the speed is recovered but only to the extent allowed by the inherent roughness of the painted hull.

We have found an anti-fouling paint composition which at least preserves the ship's service efficiency during the life of the top coat paint and which may in some circumstances lead to an improvement in that efficiency during service.

According to the present invention a top coat paint for ships' hulls comprises:

a. a film-forming copolymer containing from more than 50 up to 80 percent by weight of units of at least one triorgano tin salt of an olefinically unsaturated carboxylic acid, the balance of the copolymer being units of at least one olefinically unsaturated comonomer;

b. a substantially water insoluble metalliferous pigment capable of reacting with sea-water to form a water-soluble metal compound, and c. a hydrophobic organic retarder for retarding the rate of ion exchange between sea-water and the copolymer (a), which retarder
  i. has a solubility in sea-water at 25° C of not more than 5 parts per million by weight and is miscible with the copolymer (a),
  ii. has a negligible vapour pressure at 25° C, and
  iii. is present to the extent of at least 5 percent by weight based on the weight of the tri-organo tin ion content of the copolymer (a).

The top coat paint according to the invention exhibits the anti-fouling action to be expected from its ability to release organo tin ions into sea-water. However, a unique property of the paint revealed in dynamic tests in which painted rotors were revolved in sea-water at speeds of up to 40 knots, is that the sea-water planes the surface, removing excrescences composed of the paint. We have, for example, purposely roughened the surface of such a panel by combing the partially dried paint film to give a 50 $\mu$m roughness, and achieved a smooth film again within a month on the rotor test at a speed of 20 knots. These observations have now been confirmed by panels painted on ships — the panels have become smoother during the ordinary traffic of the ship and with no other assistance.

Figure 2A:
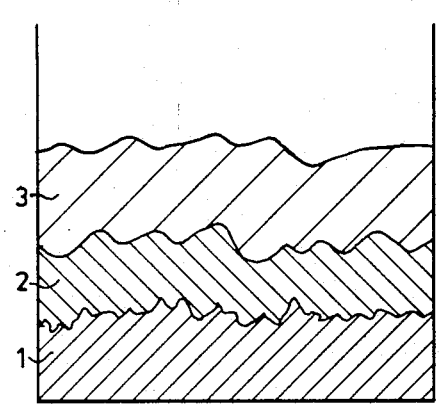
Figure 2B:
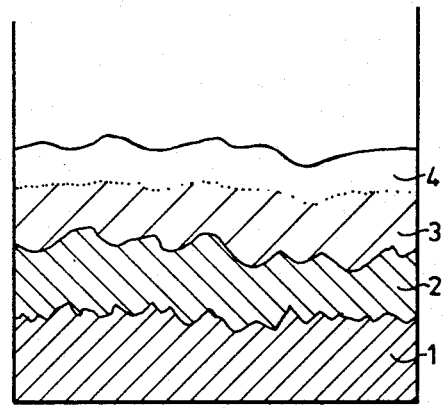

This difference in the performances of the top coat paint according to the invention and a conventional anti-fouling paint is illustrated in FIGS. 2A–2D of the drawings. All of these four figures are cross-sectional views through part of the hull of a ship showing the steel plate 1, the anti-corrosive paint 2 and the anti-fouling paint 3. FIG. 2A represents a newly painted hull using a known anti-fouling coating and FIG. 2B shows the same coating near the end of its useful life, say after 18 months, where the anti-fouling agent dispersed in the film-forming matrix has been leached from the coating by sea-water to a depth shown as a dotted line between the regions 3 and 4. The outermost region 4 overlies the potentially useful anti-fouling region 3, inhibiting the leaching of anti-fouling agent in lethal concentrations from that region to the outer surface of region 4 so that fouling ensues.

Figure 2C:
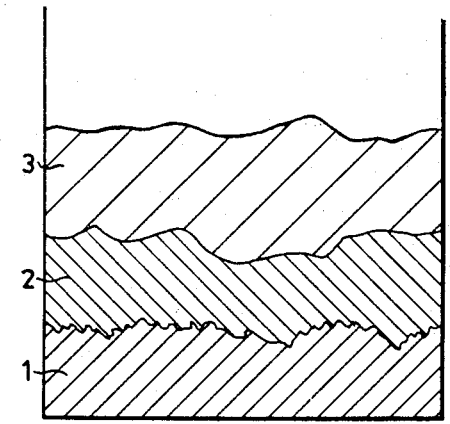
Figure 2D:
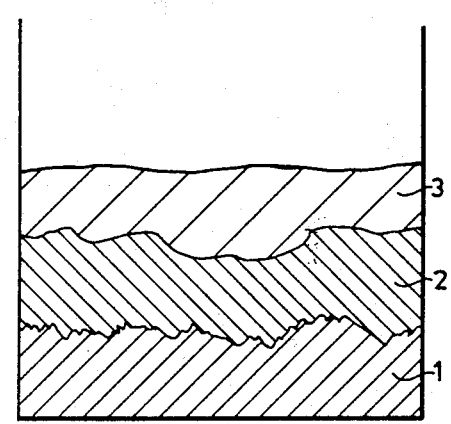

FIG. 2C represents a ship freshly painted with a top coat paint 3 according to this invention. Over a period, the top coat paint 3 is planed by the sea-water, becoming thinner and smoother as shown in FIG. 2D, yet the anti-fouling capability is unchanged and no inactive surface develops to hinder the release of the biocide.

The observation that ionic copolymers containing tri-organo tin ions are effective as anti-fouling agents, is not new. Such copolymers have been proposed, for example in British patent specification No. 1,058,701 (U.S. Pat. No. 3,167,473). It is also understood that certain of these copolymers become water-soluble when depleted of their tri-organo tin content by ion exchange with sea-water. We have found that the copolymers alone, or mixtures thereof with inert pigments, do not exhibit the selective planing by sea-water which characterises the top coat paint of this invention, but rather are subject to localised erosion which contributes to, rather than lessens, the frictional drag on the ship.

Upon contact with sea-water, the copolymer in paints according to the invention generates a water-soluble residue which essentially is a copolymer salt formed as a result of the depletion in the copolymer organo tin content caused by exchange of tin ions for metal ions present in the sea-water. It has been found that the copolymer must contain more than 50 percent by weight of organo tin salt units in order to generate the water-soluble residue at a sufficient rate. If the organo tin content of the copolymer is less than about 50 percent, the organo tin ion may still be exchanged with a metal ion from sea-water, but the residual polymer either separates from the ship's hull in a way which does not lead to a smoother surface, or remains upon the hull. In the latter case the paint behaves similarly to the known anti-fouling paints as described with reference to FIGS. 2A and 2B.

The more the organo tin salt content of the copolymer exceeds 50 percent by weight, the greater the rate of ion exchange with sea-water and the quicker the copolymer becomes water-soluble enough to be swept away from the paint surface by the sea-water flowing over the surface. Such a copolymer as a varnish (i.e. mixed with no other permanent component in the coating), exhibits localised and random thinning of the coat and the overall smoothness of the coat is not reproducibly improved. Neither is the smoothness improved when an inert pigment, for example titanium dioxide, is incorporated in the film.

The substantially water-insoluble pigments of this invention on the other hand produce water-soluble metal compounds on reaction with sea-water so that the pigment particles do not survive at the paint surface. The pigment also has the effect of inducing the overall planing which the relatively moving sea-water exerts on the paint film, minimising the localised erosion mentioned earlier in the context of known anti-fouling compositions. This important benefit is not easily explained. Preferably, the pigment is present in an amount of at least 2.5 parts by weight per part by weight of the copolymer.

The combination of a copolymer containing more than 50 percent by weight of organo tin salt and the sea-water reactive pigment is itself an anti-fouling paint but of such short service life due to its rate of dissolution in relatively moving sea-water, as to be uneconomic. We have found that the service life of the film may be remarkably and adjustably extended by incorporating in the paint a hydrophobic retarder as defined. The proportion of the retarder in the composition must be at least 5 percent by weight of the tri-organo tin ion content of the copolymer in the paint to achieve a minimum economic life expectancy for the paints; higher proportions of the retarder prolong that expectancy. It is likely that the retarder limits the rate of loss of the tri-organo tin ion from the paint film, but whatever the mechanism, the ternary composition of this invention — organo tin salt copolymer, a pigment reactive with sea-water and the hydrophobic non-volatile retarder — is an anti-fouling paint of adequate life having the valuable additional property of at least not causing an increase in the frictional drag of the ship's hull during its service life.

The tri-organo tin salt of the olefinically unsaturated carboxylic acid incorporated in the copolymer suitably has the general formula

where R is the same or different alkyl radicals containing up to 8 carbon atoms or aryl or aralkyl radical, R' is H or methyl and R" is H, or — COOSn R$_3$. Thus the cation of the salt, R$_3$Sn$^+$, is exemplified by tributyl tin, tripropyl tin, triethyl tin, tribenzyl tin, diethylbutyl tin, diethylamyl tin, diamylmethyl tin, triphenyl tin, tribromophenyl tin, diphenyltolyl tin, tritolyl tin, diethyl phenyl tin, ethyl diphenyl tin, octyldiphenyl tin and diethyloctyl tin. The preferred cations are those having three identical organic groups attached to the tin atom. The anion of the salt, —OOCCR'=CHR", may be, for example, acrylate, methacrylate, maleate or fumarate. Examples of the salt come from pairing any listed anion with any listed cation.

The copolymer also contains at least one ethylenically unsaturated comonomer. Substances suitable as comonomers are acrylic monomers, for example methyl methacrylate, ethyl acrylate, propyl acrylate, amyl acrylate, hexyl acrylate and the corresponding esters of methacrylic acid; acrylonitrile, methacrylonitrile, acrylamide and methacrylamide; and vinyl monomers, for example, vinyl acetate, vinyl butyrate, vinyl chloride, styrene and vinyl pyridine.

The copolymer preferably comprises methacrylate salts of the tri-organo tin and methacrylate and/or acrylate esters as the comonomers.

The substantially water insoluble pigment reactive with sea-water is exemplified by zinc oxide, cuprous thiocyanate, copper acetoarsenite, cuprous oxide and zinc chromate.

The retarder is an organic compound with a water solubility of less than 5 parts per million by weight. The organic compounds set out in the following List A, whilst well-known as plasticisers and common components of paint vehicles, are not retarders:

| List A - Solubility in sea-water (p.p.m. by weight) | |
| --- | --- |
| Sextol phthalate | >50 |
| Di 2 ethyl hexyl phthalate | >100 |
| Dibutyl phthalate | >100 |
| Tritolyl phosphate | 20 |
| Di iso butyl tartrate | 104 |
| Di butyl tartrate | 104 |
| Iso butyl nonyl phthalate | >50 |
| Di iso butyl phthalate | 100 |
| Triamyl citrate | >200 |

The compounds of List B are examples of retarders and these are all hydrophobic materials of very low sea-water solubility:

| List B - Solubility in sea-water (p.p.m. by weight) | |
| --- | --- |
| Methyl phenyl silicone fluid (Silicone Fluid DC 550 ex Dow-Corning Ltd.) | <1 |
| Chlorinated diphenyl (Aroclor 1254 ex Monsanto Ltd.) | <2 |
| Chlorinated paraffin wax | |
| (a) Cereclor 48 ex I.C.I. Ltd.) | <5 |
| (b) Cereclor 70 ex I.C.I. Ltd.) | <5 |
| Naphthalene | <5 |
| Diphenyl ether | <5 |
| Dichlorodiphenyl trichloroethane | <1 |
| Low molecular weight polybutene (Hyvis 05 ex B.P. Ltd.) | <5 |

All these compounds have a negligible vapour pressure at 25° C; in other words they are non-volatile at ordinary temperatures.

The miscibility of a candidate retarder and the copolymer may be tested by dissolving the candidate and the copolymer in a common solvent, spreading the solution as a thin film on a glass plate and removing the solvent to leave a solid film having a thickness of between 1 and 2 μm. If the film appears to the eye to have a single phase in transmitted light, the retarder is miscible with the copolymer for the purposes of this invention; the candidate would fail if there was visible phase separation.

One or more such hydrophobic retarders may be employed in the top coat paint composition.

The benefit of this invention is best brought out in applying the top coat composition in two or more coats, say three or four, to the hull and increasing the susceptibility of the coats to the planing action of the sea-water from the first applied to the last coat. Thus the first applied coating should have the largest proportion of hydrophobic retarder in its composition, say between 60 and 120 percent of the weight of the triorgano tin ion content of the composition. The next coat may have from, say, 20 to 50 percent and the outer coat the minimum of 5 percent. Thus the outer coat is planed early in the service life of the painted ship and the subsequent coats later and more slowly ensuring an adequate anti-fouling performance whilst obtaining early on the rewards of a smoothed hull.

Preferably the organo tin salt component forms from 55 to 65 percent by weight of the copolymer and the ion exchange properties of such copolymers in combination with more or less of the retarder may be controlled to provide respectively paints which are the least susceptible and most susceptible to the planing action of sea-water likely to be required in practice.

The invention is illustrated by the following Examples in which parts and percentages are by weight unless otherwise stated.

EXAMPLE 1 a. Preparation of Copolymers containing Triorgano Tin Salts

Five copolymers of tributyl tin methacrylate and methyl methacrylate were made from the mixtures of monomers shown in Table I.

TABLE I

| Copolymer | A | B | C | D | E | |
| --- | --- | --- | --- | --- | --- | --- |
| Tributyl tin methacrylate | 50 | 55 | 60 | 65 | 70 | parts |
| Methyl methacrylate | 50 | 45 | 40 | 35 | 30 | parts |

The same procedure was followed in polymerising each mixture, namely, 40 parts of the mixture of monomers was dissolved in 60 parts of xylene in a reaction vessel equipped with means to heat and to cool the contents and 0.35 part of benzoyl peroxide was added. The temperature of the solution was raised gradually over 10 hours, employing the cooling means as necessary to control the exotherm, to a final temperature of 110° C under reflux. The final solution viscosity was in the range 3 to 6 poises at 25° C.

b. Paints i. Paints omitting retarder

The Copolymers A, B, C, D and E were individually blended with other paint constituents as follows:
36.1 parts of a 40 percent solution of the copolymer in xylene
34.93 parts of ZnO
10.92 parts of acicular ZnO
0.7 parts of colloidal silica
0.9 parts of bentonite
0.4 parts of tributyl tin oxide
12.4 parts of xylene.

Finally, the formulation was adjusted to a solids content of 31.2 percent by volume, by the addition of xylene.

Figure 7A:
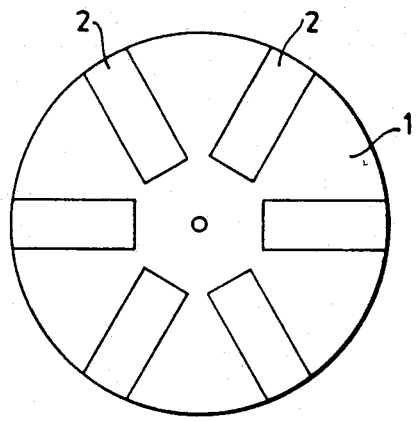
Figure 7B:
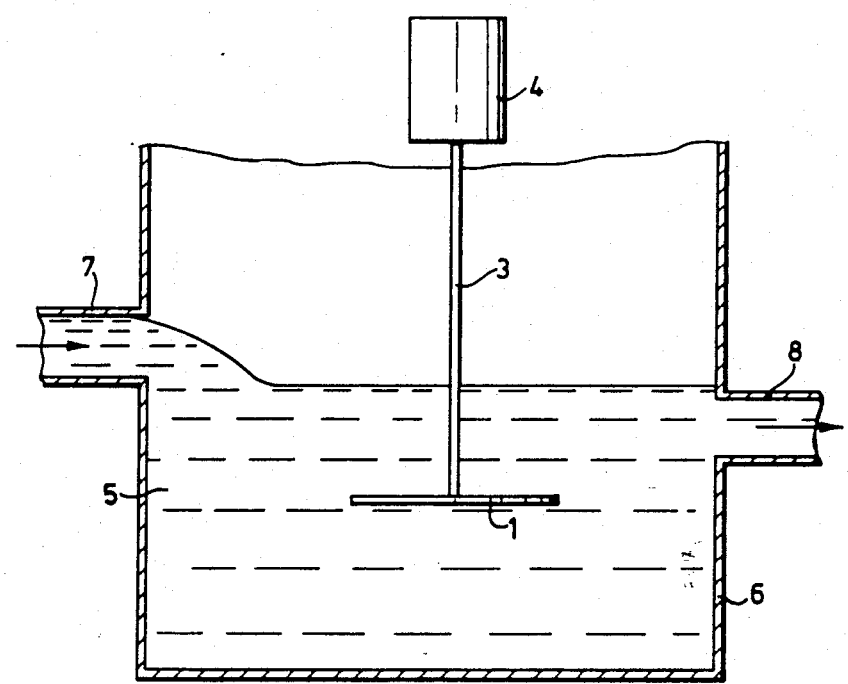

Rotor Test — The performance of the paints in relatively moving sea-water was tested in the apparatus illustrated schematically in FIGS. 7A and 7B of the drawings. Referring to these Figures, a mild steel disc 1 having a diameter of 23 cms was coated overall with a conventional anti-fouling paint and overcoated in radial stripes 2 with the paints under test applied from an applicator adapted to deposit a film of 20 μm thickness. The disc 1 was set aside to dry and the thickness of the stripes 2 was measured using the B.S.R.A's Wall Gauge: all should theoretically have been 6¼ μm thick, but variations amounting to ± ½ μm (which limits represent the measuring accuracy of the gauge) were found in some areas of some stripes 2.

The disc 1 was mounted on a shaft 3 driven by an electric motor 4 and immersed in flowing sea-water 5 contained in a vessel 6 having an inlet 7 and an overflow 8. The peripheral speed of the disc 1 was 38 knots.

During this test, the stripes were planed away from the disc, in some cases to the extent that the underlying anticorrosive paint was revealed. The rate of removal was measured for each stripe: the plot of this rate against the period of rotation shows a slightly accelerating rate early in test and a decelerating rate later in the test. From such plots it is possible to note or to extrapolate the 50 D value (days of test elapsed for the loss of 50 percent of the top coat paint film from the panel).

Figure 3:
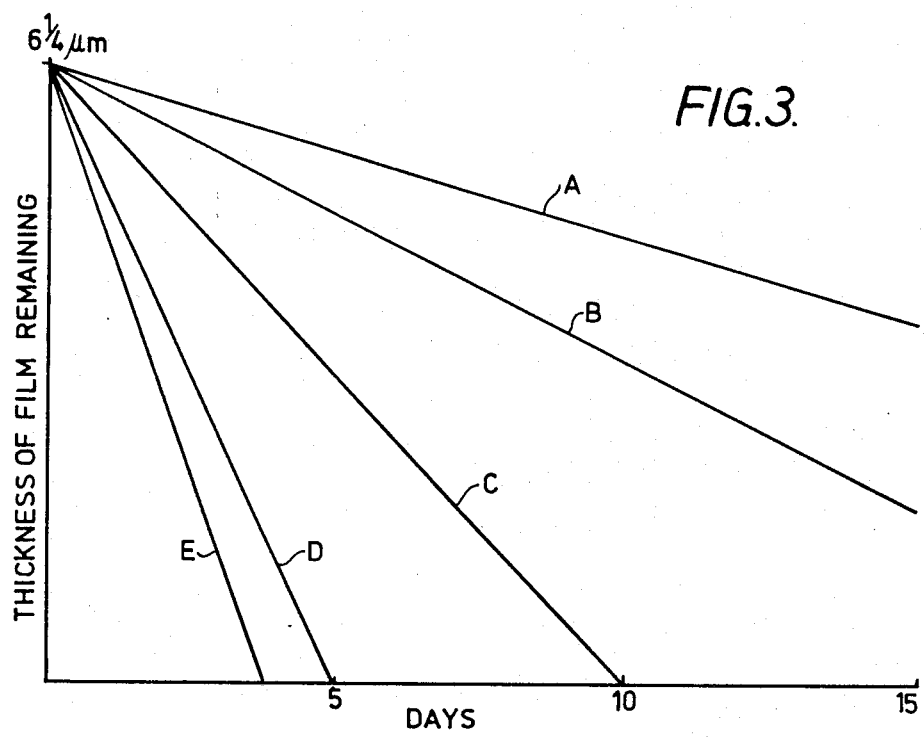

The results of the rotor testing of the paints omitting the retarder are shown in FIG. 3, the performance of a paint being identified by the code letter of the copolymer it contains: the periods of accelerating and decelerating loss which we noted and which would lead to slight curvatures in the plot, have been ignored as being within the limits of accuracy of the routine test and the rate of loss in each case is shown as constant. The importance of the test results in the demonstrated difference in the susceptibility of paints to planing by sea-water. Thus the paint containing Copolymer A (50 parts methyl methacrylate/50 parts tributyl tin methacrylate) had the smallest rate of loss (line A of FIG. 3) and in line with the increasing organo tin salt concentration in the Copolymers B, C, D and E show increasing rates of loss.

None of the paints shows an ideal rate of planing and the large differences in the rates due to relatively small changes in the compositions of the copolymers does not suggest that a commercial paint of reproducible planing properties can be formulated without a retarder.

There is no known method of accelerating the loss of paint by planing and the rate of loss of the paint containing Copolymer A is too slow (and has an inefficient anti-fouling performance, see this Example (c) (ii)).

ii. Paints containing Retarder

Five paints were made according to the formulation in (b) (i), of this Example using Copolymer C in all five: dichlorodiphenyl trichloroethane, the retarder, was added in varying amounts to four of the five paints as shown in Table 2.

| Paints | 1 | 2 | 3 | 4 | 5 |
|---|---|---|---|---|---|
| Dichlorodiphenyl trichloroethane | 0 | 15 | 30 | 60 | 120* |

*percent of dichlorodiphenyl trichloroethane based on the organo tin content of Copolymer C.

Figure 4:
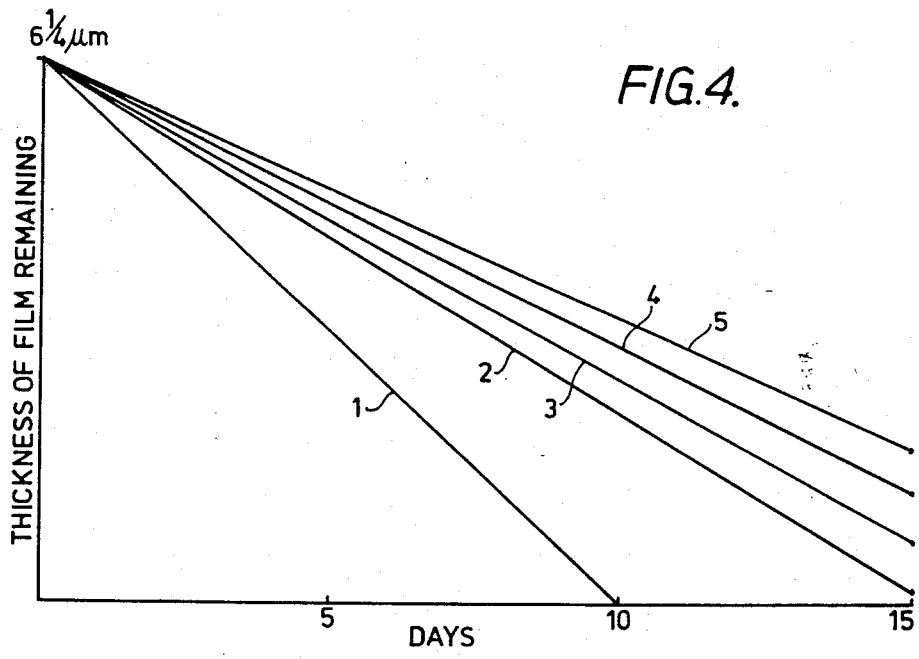

The paints were submitted to the rotor test as described and the results are shown in FIG. 4, the plots being identified by the paint numbers. It will be seen that the presence of dichlorodiphenyl trichloroethane retards the rate of planing of the paint coating and that the effect increases with the concentration of the retarder.

Figure 6:
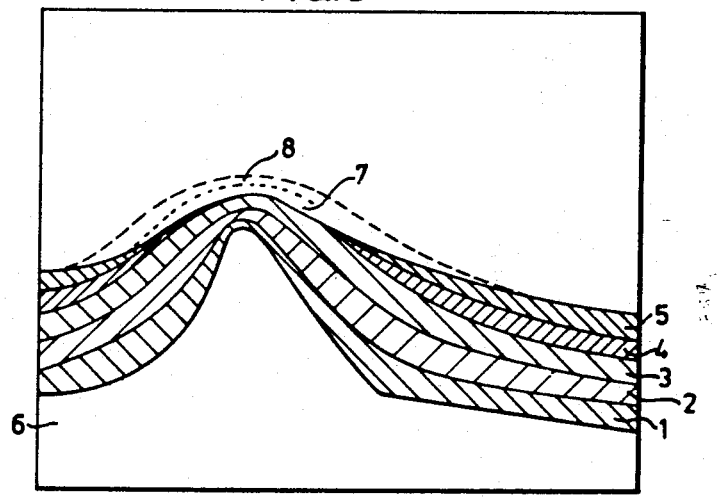

The retarder may be employed in proportions to compensate for batch-to-batch variations of a chosen copolymer to enable the manufacture of batches of paint having a specified planing rate, or to formulate paints having a range of planing rates, all based on a single copolymer.

c. Ship Trials i. Paint 4 of (b) (ii) of this Example was applied in four coats each of a dry thickness of 75 $\mu$m to a panel; the surface of the final coat had a roughness of 85 $\mu$m measured by the B.S.R.A.'s Wall Gauge. The panel was fixed to the bilge keel of a tanker and after 14 months was found to be free from fouling. Moreover, the paint surface was so smooth that the Wall Gauge could not detect a measurable roughness. The paint had been planed at a rate of approximately 10 $\mu$m/month.

ii. The same tanker also carried panels similarly painted with a Paint 1 containing Copolymer A instead of Copolymer C. This paint was not smoother at the end of 14 months and had not inhibited fouling.

iii. Paint 4, omitting the retarder, was carried on panels on the same tanker. The panel was free from fouling, but the rate of loss of the paint thickness was excessive at approximately 300 $\mu$m/year.

iv. Eight areas of the same tanker's hull were painted with Paint 4 in five coats of different colours to a total dry coat thickness of 300 $\mu$m. These areas remained free from fouling and were planed in the same way and to the same degree as the panels. However, the paint was applied over an already rough paint surface and within 2½ months of the normal traffic of the vessel the areas showed isolated dots of the third and fourth coat colours showing through the fifth (top) coat colour. Sections of these dots were taken and the structure found is shown in FIG. 6. The five coats of the top coat paint of this invention are numbered 1 to 5; they cover old paint and a conical protuberance 6. It will be seen that the outermost coat 5 has been planed by the seawater preferentially at the tip and shoulders of the protuberance 6 and that the next inner coat 4 has also been planed at the tip. The original state of coats 4 and 5 is suggested by the zones 7 and 8 defined by dotted and broken lines 9 and 10.

The preferential planing of excrescences of the paint demonstrates how the top coat paint of this invention may to an extent compensate even for the gross roughness of the surface to which it is applied.

v. A paint formulated as Paint 4 of (b) (ii) of this Example but employing as the copolymer component, Component D (instead of Copolymer C), was applied as four coats to four rectangular panels each of 30 × 20 cm. The dry coat thickness was 300 $\mu$m in each case.

All four panels were attached to the bilge keel of a very large crude-oil carrier and one panel was removed after 9 months, another after 13 months, the third after 18 months and the last at 22 months.

The initial roughness of all panels was in the range 75 to 90 $\mu$m: after the trial all were so smooth that the B.S.R.A.'s Wall Gauge could measure no roughness. Paint had been removed from the panels at the rate of about 12 $\mu$m per month and all were free from fouling. Panels similarly painted with conventional anti-foulings and mounted with the test panels were fouled with green and brown seaweeds from 13 months onwards and a panel having a coating with no anti-fouling properties was fouled within 9 months.

vi. The paint tested on the crude-oil carrier was also applied in two 100 $\mu$m coats to the sides of a tanker and examined 6 months later. The flat bottom and 2 meters above the anti-fouling line were completely fouled with barnacles and tube worms, except for the area of the test coat which was completely free from fouling.

EXAMPLE 2

Figure 5:
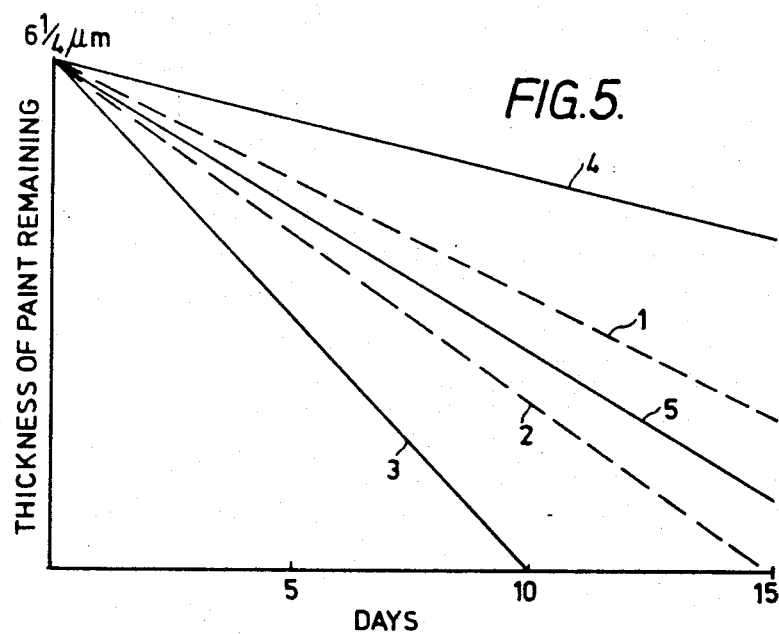

The retarders of List B were individually incorporated as replacements for dichlorodiphenyl trichloroethane in paints made by the process and formulation of Paint 3 of Example 1 (b) (ii). The paints were submitted to Rotor Testing as described in Example 1 and the rates of loss showed remarkably little difference due to changes in the nature of the retarder. FIG. 5 summarises these findings: all the paints showed a rate of loss falling in the area contained by the broken lines 1 and 2; the rate of loss 3 of the paint containing no retarder and the performance 4 of a paint based on the Copolymer A and no retarder are included for comparison. Plot 5 is the rate of loss of Paint 3 already recorded in FIG. 4.

EXAMPLE 3

TABLE 3

| | F | G | H | J | K | L | M | N |
|---|---|---|---|---|---|---|---|---|
| Tributyl tin methacrylate | 60 | 30 | | | 30 | 30 | 60 | 30 |
| Tri-isopropyl tin methacrylate | | 30 | | 30 | | 30 | | |
| Triamyl tin acrylate | | | 60 | 30 | 20 | | | 30 |
| Triphenyl tin acrylate | | | | | 10 | | | |
| Methyl methacrylate | 40 | 20 | 10 | | | | 20 | 20 |
| Methyl acrylate | | | | 30 | | 10 | | |
| Ethyl Methacrylate | | 20 | | | | 20 | | 20 |
| Hexyl acrylate | | | | 10 | | | | |
| Styrene | | | | | | 30 | 10 | |
| 4-Vinyl pyridine | | | | | 10 | 10 | | |
| Acrylonitrile | | | | | | | | 40 |

Eight copolymers having compositions disclosed in Table 3 and paints incorporating them were made in accordance with the processes described in Example 1. There was no significant difference in the properties of the paints, but slight variations in the qualities of the dried coats were apparent: in general the films having a substantial proportion of methyl methacrylate, styrene or vinyl pyridine were firmer rubbery materials than those in which the comonomer was an acrylate ester or acrylonitrile. In the Rotor Test of painted panels, the paints all showed the same performance in combination with increasing proportions of dichlorodiphenyl trichloroethane namely a reduction in the rate of planing of the coating in relatively moving sea-water, following closely the results indicated in FIG. 4.

What is claimed is:
1. A top coat paint for ships' hulls comprising
   a. a film-forming copolymer containing from more than 50 up to 80 percent by weight of units of at least one tri-organo tin salt of an olefinically unsaturated carboxylic acid having the general formula $R_3SnOOCCR' = CHR''$ where R is the same or different alkyl radical containing up to 8 carbon atoms, an aryl group or an aralkyl group, R' is hydrogen or a methyl group and R'' is hydrogen or a —$COOSnR_3$ group, the balance of the copolymer being units of at least one olefinically unsaturated comonomer,
   b. a substantially water insoluble metalliferous pigment capable of reacting with sea-water to form a water-soluble metal compound, and
   c. a hydrophobic organic retarder for retarding the rate of ion exchange between sea-water and the copolymer (a), which retarder
      i. has a solubility in sea-water at 25° C of not more than 5 parts per million by weight and is miscible with the copolymer (a),
      ii. has a negligible vapour pressure at 25° C, and
      iii. is present to the extent of 5 to 120 percent by weight based on the weight of the tri-organo tin ion content of the copolymer (a), and
   d. an organic solvent for components (a) and (c).

2. A top coat paint as claimed in claim 1 wherein the triorgano tin salt is tributyl tin methacrylate.

3. A top coat paint as claimed in claim 1 wherein the comonomer in (a) consists of or comprises an ester of acrylic or methacrylic acid.

4. A top coat paint as claimed in claim 3 wherein the comonomer consists of methyl methacrylate.

5. A top coat paint as claimed in claim 1 wherein the triorgano tin salt forms from 55 to 65 percent of the copolymer (a).

6. A top coat paint as claimed in claim 1 wherein the pigment is present in an amount of at least 2.5 parts by weight per part by weight of the copolymer (a).

7. A top coat paint as claimed in claim 6 wherein the retarder (c) is selected from the group consisting of methyl phenyl silicone fluid, chlorinated diphenyl, chorinated paraffin was, naphthalene, diphenyl ether, dichlorodiphenyl trichloroethane and low molecular weight polybutene.

8. A top coat paint as claimed in claim 1 wherein the retarder is dichlorodiphenyl trichloroethane.

9. A top coat paint as claimed in claim 1 wherein the metalliferous pigment is zinc oxide.

* * * * *